United States Patent
Ramakrishnan et al.

(10) Patent No.: US 12,123,038 B2
(45) Date of Patent: Oct. 22, 2024

(54) PROTIC OR PHOSPHATE-BASED IONIC LIQUIDS USEFUL FOR LIGNOCELLULOSIC PROCESSING

(71) Applicant: National Technology & Engineering Solutions of Sandia, LLC, Albuquerque, NM (US)

(72) Inventors: Parthasarathi Ramakrishnan, Lucknow (IN); Jian Sun, Albany, CA (US); Tanmoy Dutta, Berkeley, CA (US); Blake A. Simmons, San Francisco, CA (US); Seema Singh, Clarksburg, MD (US)

(73) Assignee: NATIONAL TECHNOLOGY & ENGINEERING SOLUTIONS OF SANDIA, LLC, Albuquerque, NM (US)

( * ) Notice: Subject to any disclaimer, the term of this patent is extended or adjusted under 35 U.S.C. 154(b) by 232 days.

(21) Appl. No.: 16/284,941

(22) Filed: Feb. 25, 2019

(65) Prior Publication Data
US 2019/0292572 A1    Sep. 26, 2019

Related U.S. Application Data

(63) Continuation of application No. PCT/US2017/048507, filed on Aug. 24, 2017.

(60) Provisional application No. 62/379,043, filed on Aug. 24, 2016.

(51) Int. Cl.
| | | |
|---|---|---|
| C12P 19/02 | (2006.01) | |
| C08F 251/02 | (2006.01) | |
| C08L 97/00 | (2006.01) | |
| C12P 7/10 | (2006.01) | |
| C12P 19/14 | (2006.01) | |

(52) U.S. Cl.
CPC ............ *C12P 19/02* (2013.01); *C08F 251/02* (2013.01); *C08L 97/00* (2013.01); *C12P 7/10* (2013.01); *C12P 19/14* (2013.01); *C12P 2201/00* (2013.01)

(58) Field of Classification Search
None
See application file for complete search history.

(56) References Cited

U.S. PATENT DOCUMENTS

| | | | |
|---|---|---|---|
| 8,182,557 B2 | 5/2012 | Argyropoulos | |
| 10,703,770 B2 * | 7/2020 | Sun | C12P 7/10 |
| 10,907,182 B2 * | 2/2021 | Yang | C12N 9/90 |
| 2012/0010334 A1 | 1/2012 | D'Andola et al. | |
| 2013/0245252 A1 | 9/2013 | Makkee et al. | |
| 2016/0053407 A1 | 2/2016 | Michud et al. | |

FOREIGN PATENT DOCUMENTS

DE   102011083362 A1   3/2012

OTHER PUBLICATIONS

Holm et al. (Ionic Liquids: Application and Preparations, 2011, pp. 545-559).*
Wang et al., "Ionic liquid processing of cellulose", Chemical Society Reviews, 41:1519-1537 (2012).
Himmel et al., "Biomass Recalcitrance: Engineering Plants and Enzymes for Biofuels Production", Science, 315: 804-807 (2007).
Mosier et al., "Features of promising technologies for pretreatment of lignocellulosic biomass" Bioresource Technol, 96, 673-686 (2005).
Hallett et al., "Room-Temperature Ionic Liquids: Solvents for Synthesis and Catalysis. 2", Chemical Reviews, 111: 3508-3576 (2011).
Shi et al., "Impact of mixed feedstocks and feedstock densification on ionic liquid pretreatment efficiency", Biofuels, 4, 63-72 (2013).
Li et al., Scale-up and evaluation of high solid ionic liquid pretreatment and enzymatic hydrolysis of switchgrass Biotechnology for Biofuels, 2013, 6:154 (2013), 13 pages.
Da Silva et al., "Continuous pretreatment of sugarcane bagasse at high loading in an ionic liquid using a twin-screw extruder" Green Chemistry, 15:1991-2001 (2013).
Shi et al, "One-pot ionic liquid pretreatment and saccharification of switchgrass" Green Chem, 15:2579-2589 (2013).
Quijano et al., "Ionic liquids: Applications and future trends in bioreactor technology". Bioresource Technol, 101:8923-8930 (2010).
Tang et al., "Ether- and alcohol-functionalized task-specific ionic liquids: attractive properties and applications" Chemical Society Reviews, 41:4030-4066 (2012).
Park et al., "A Thermophilic Ionic Liquid-Tolerant Cellulase Cocktail for the Production of Cellulosic Biofuels" Plos One, 7:e37010 (2012), 10 pages.
Gladden et al., Discovery and characterization of ionic liquid-tolerant thermophilic cellulases from a switchgrass-adapted microbial community, Biotechnol Biofuels, 7:15 (2014), 12 pages.
Sun et al., "Understanding pretreatment efficacy of four cholinium and imidazolium ionic liquids by chemistry and computation" Green Chem, 6:2546-2557 (2014).
Chen et al., Inexpensive ionic liquids: [HSO4]-based solvent production at bulk scale, Green Chem, 16:3098-3106 (2014).
Ohira et al., "Design of Cellulose Dissolving Ionic Liquids Inspired by Nature", ChemSusChem, 5:388-391 (2012).
Tomé et al., "Cholinium-based Supported Ionic Liquid Membranes: A Sustainable Route for Carbon Dioxide Separation" ChemSusChem, 7:110-113 (2014).
Liu et al., "Ionic liquids from renewable biomaterials: synthesis, characterization and application in the pretreatment of biomass", Green Chem, 14: 304-307 (2012).

(Continued)

*Primary Examiner* — Hope A Robinson
(74) *Attorney, Agent, or Firm* — Robin C. Chiang; LAWRENCE BERKELEY NATIONAL LABORATORY

(57) ABSTRACT

The present invention provides for novel protic ionic liquids (PIL) or phosphate-based ionic liquid (PBIL) useful for lignocellulosic processing described herein. The novel protic ionic liquids are capable of pretreatment of lignocellulosic biomass over a wide range of pH.

12 Claims, 13 Drawing Sheets

(56) References Cited

OTHER PUBLICATIONS

Fukaya et al., "Bio ionic liquids: room temperature ionic liquids composed wholly of biomaterials" Green Chem, 9: 1155-1157 (2007).
Yuan et al., "Hydroxyl Ammonium Ionic Liquids: Synthesis, Properties, and Solubility of SO2", Journal of Chemical & Engineering Data, 52: 596-599 (2007).
Yuan et al., "Solubilities of CO2 in hydroxyl ammonium ionic liquids at elevated pressures" Fluid Phase Equilibria, 257: 195-200 (2007).
Sun et al., "Hydroxyl-functionalized ionic liquid: a novel efficient catalyst for chemical fixation of CO2 to cyclic carbonate", Tetrahedron Letters, 49: 3588-2591 (2008).
Zhai et al., "Hydroxyl ammonium ionic liquids synthesized by water-bath microwave: Synthesis and desulfurization" Journal of Hazardous Materials, 177:807-813 (2010).
Guo et al., "Solubility of SO2 in Caprolactam Tetrabutyl Ammonium Bromide Ionic Liquids", Journal of Chemical & Engineering Data, 55:1398-1401 (2009).
Cui et al., "Highly efficient SO2 capture by dual functionalized ionic liquids through a combination of chemical and physical absorptionw", Chemical Communications, 48: 2633-2635 (2012).
Ismail et al., "Synthesis and anti-microbial activity of hydroxylammonium ionic liquids", Chemosphere, 84: 101-104 (2011).
Brandt et al., "The effect of the ionic liquid anion in the pretreatment of pine wood chips", Green Chem, 12: 672-679 (2010).
Parviainen et al., "Predicting Cellulose Solvating Capabilities of Acid-Base Conjugate Ionic Liquids", Chemsuschem, 6: 2161-2169 (2013).
Hauru et al., "Role of Solvent Parameters in the Regeneration of Cellulose from Ionic Liquid Solutions", Biomacromolecules, 13: 2896-2905 (2012).
Greaves et al., "Protic Ionic Liquids: Properties and Applications", Chemical Reviews, 108: 206-237 (2008).
Poole, "Chromatographic and spectroscopic methods for the determination of solvent properties of room temperature ionic liquids" J Chromatogr A, 1037: 49-82 (2004).
Gladden et al., "Glycoside Hydrolase Activities of Thermophilic Bacterial Consortia Adapted to Switchgrass" Appl Environ Microb, 77: 5804-5812 (2011).
Turner et al., "Ionic liquid salt-induced inactivation and unfolding of cellulase from Trichoderma reesei" Green Chem, 5: 443-447 (2003).
Wada et al., "Thermally Induced Crystal Transformation from Cellulose Iα to Iβ", Polym J, 35: 155-159 (2003).
Cheng et al., "Transition of Cellulose Crystalline Structure and Surface Morphology of Biomass as a Function of Ionic Liquid Pretreatment and Its Relation to Enzymatic Hydrolysis" Biomacromolecules, 12: 933-941 (2011).
Remsing et al., "Mechanism of cellulose dissolution in the ionic liquid 1-n-butyl-3-methylimidazolium chloride: a 13C and 35/37Cl NMR relaxation study on model systems" Chemical Communications, 1271-1273 (2006).
Wyman et al., "Fundamentals of Production from Renewable Feedstocks and use as a Transportation Fuel", Appl Biochem Biotech, 24/5, 735-736 (1990), abstract.
Xu et al., "Transforming biomass conversion with ionic liquids: process intensification and the development of a high-gravity, one-pot process for the production of cellulosic ethanol", Energy & Environmental Science, 9:1042-1049 (2016).
International Search Report and Written Opinion for PCT/US2017/048507, Nov. 9, 2017.

\* cited by examiner

PROTIC OR PHOSPHATE-BASED IONIC LIQUIDS USEFUL FOR LIGNOCELLULOSIC PROCESSING

CROSS-REFERENCE TO RELATED APPLICATIONS

This application claims priority as a continuation application to PCT International Patent Application No. PCT/US2017/048507, filed Aug. 24, 2017, which claims priority to U.S. Provisional Patent Application Ser. No. 62/379,043, filed Aug. 24, 2016, both of which are incorporated by reference in their entireties.

STATEMENT OF GOVERNMENTAL SUPPORT

The invention was made with government support under Contract Nos. DE-AC02-05CH11231 awarded by the U.S. Department of Energy. The government has certain rights in the invention.

FIELD OF THE INVENTION

The present invention is in the field of the deconstruction of biomass using ionic liquid.

BACKGROUND OF THE INVENTION

Lignocellulosic biomass can be effectively dissolved and fractionated by imidazolium based ionic liquids (ILs). The main challenges facing IL pretreatment are the cost of ILs and system complexity associated with IL recycle, biomass solute separation and downstream processing in different pH conditions.

The practicable biorefinery depends on the cost reduction and process integration for efficient transformation of alternative fuels and chemicals from lignocellulosic biomass. Current pretreatment of biomass is achieved with relatively costly ionic liquids and at relatively severe conditions or system complexity associated with biomass solute separation and downstream processing in different pH conditions. The development of a cheap ILs which can operate at less severe pretreatment conditions, tunable pH range without additional steps and provide higher sugar yield can drastically lower the pretreatment cost.

SUMMARY OF THE INVENTION

The present invention provides for the use of a protic ionic liquids (PIL) and/or a phosphate-based ionic liquid (PBIL), or a mixture thereof useful for any pretreatment process of a lignocellulosic biomass, such as a conventional IL pretreatment, one-pot pretreatment process, aqueous phase pretreatment process, or any lignocellulosic processing described herein.

The present invention provides for compositions and methods for the making and using of PIL and/or PBIL, or mixture thereof, useful for lignocellulosic processing.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

As used in the specification and the appended claims, the singular forms "a," "an," and "the" include plural referents unless the context clearly dictates otherwise. Thus, for example, reference to an "IL" includes a single IL compound as well as a plurality of IL compounds, either the same (e.g., the same molecule) or different.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The term "about" includes a range of the value that is 10% less of the value to 10% more of the value.

Figure 1:
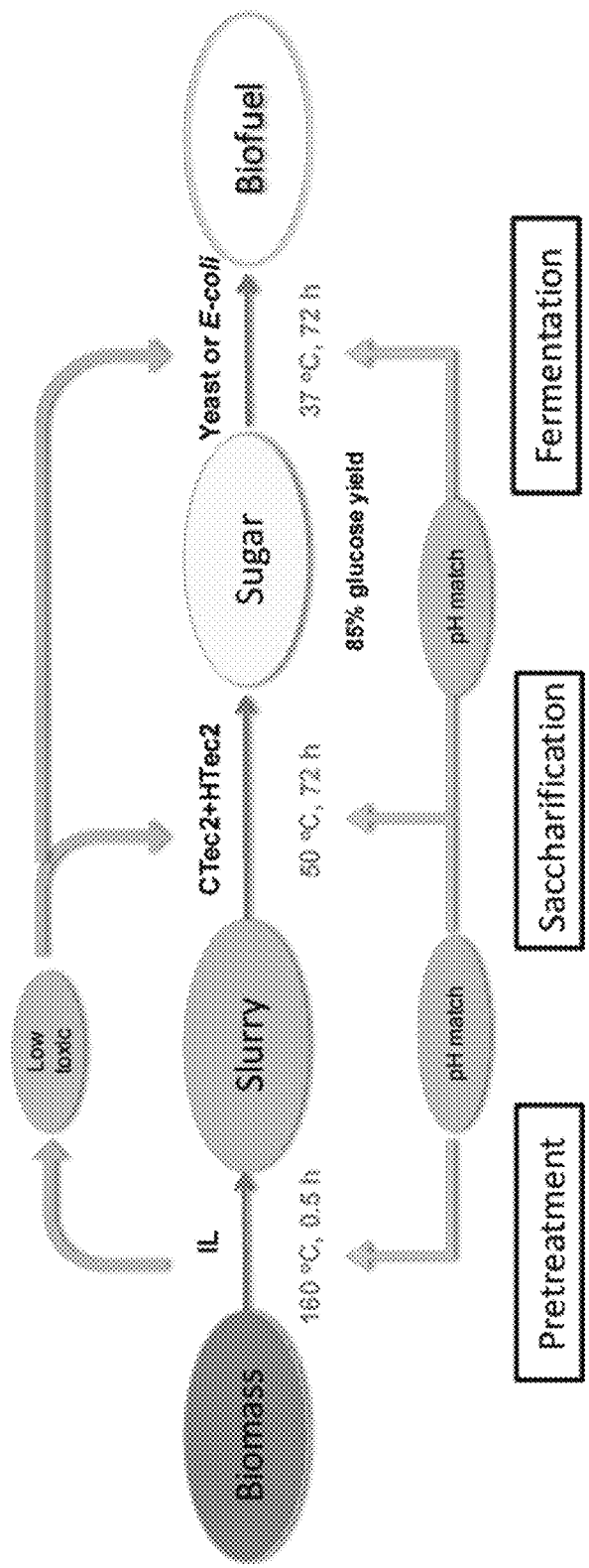
FIG. 1. One-pot integrated IL process for biofuel production.

The term "solution" is meant to also include a "slurry", such as the slurry depicted in FIG. 1.

The PIL is capable of pretreatment of lignocellulosic biomass over a wide range of pH. In some embodiments, the ILs are cholinium and/or ethanolamine based IL. The ability of the IL to pretreat lignocellulosic biomass over a wide range of pH can be optimized by tuning the anion component of the IL. Exemplary ILs of the invention are described herein.

The PIL has the following structure: [α'][β'], wherein α' is a protic substituted primary, secondary, tertiary, or quaternary alkylamine, such as an alkanol amine (such as ethanolamine or EOA), a dialkanol amine (such as diethanolamine or DEOA), a trialkanol amine (such as triethanolamine or TEOA), a cholinium, or a mixture thereof, and β' is any suitable anion, such as a phosphate-based anion (such as phosphate ($PO_4^{3-}$), hydrogen phosphate ($HPO_4^{2-}$), or dihydrogen phosphate ($H_2PO_4^-$)), an unsubstituted alkanoate (such as an ethanoate or OAc), a substituted alkanoate (such as lactate or La), a halide (such as F), a sulfate (such as $HSO_4^-$), or a mixture thereof.

The PBIL has the following structure: [α][β], wherein α is a substituted primary, secondary, tertiary, or quaternary alkylamine, such as a cholinium, an alkylamine (such as ethyl amine or EA), or an alkanol amine (such as ethanol amine or EOA), or a mixture thereof, and β is a phosphate-based anion, such as phosphate ($PO_4^{3-}$), hydrogen phosphate ($HPO_4^{2-}$), or dihydrogen phosphate ($H_2PO_4^-$), or a mixture thereof.

In some embodiments, the pretreatment process comprises the formation of a solution comprising the lignocellulosic biomass, the PIL or PBIL, and optionally a cellulase.

In some embodiments, the PIL or PBIL in the solution has a concentration having a value from about 10% to about 100%. In some embodiments, the PIL or PBIL has a concentration having a value from about 20% to about 100%. In some embodiments, the PIL or PBIL has a concentration having a value from about 50% to about 100%. In some embodiments, the PIL or PBIL has a concentration having a value of about 10%, about 20%, about 50%, and about 100%, or any value within a range of concentration of any two of the preceding percentages.

In some embodiments, the solution has a temperature of about 50° C. to about 160° C. In some embodiments, the solution has a temperature of about 10° C., about 20° C., about 30° C., about 40° C., about 50° C., about 60° C., about 70° C., about 80° C., about 90° C., about 100° C., about 110° C., about 120° C., about 130° C., about 140° C., about 150° C., and about 160° C., or any temperature within a range of any two of the preceding temperatures.

In some embodiments, the solution is a solution that has been incubated for a period of time of about 0.5 hour to about 72 hours. In some embodiments, the solution has been incubated for about 0.5 hour, about 1 hour, about 3 hours, about 12 hours, about 24 hours, about 48 hours, and about 72 hours, or any period of time within a range of any two of the preceding periods of time.

In some embodiments, the pretreatment process gives a glucose yield of equal to or more than 50%, equal to or more than 55%, equal to or more than 60%, equal to or more than 65%, equal to or more than 70%, equal to or more than 75%, equal to or more than 80%, or equal to or more than 85%.

Figure 2:
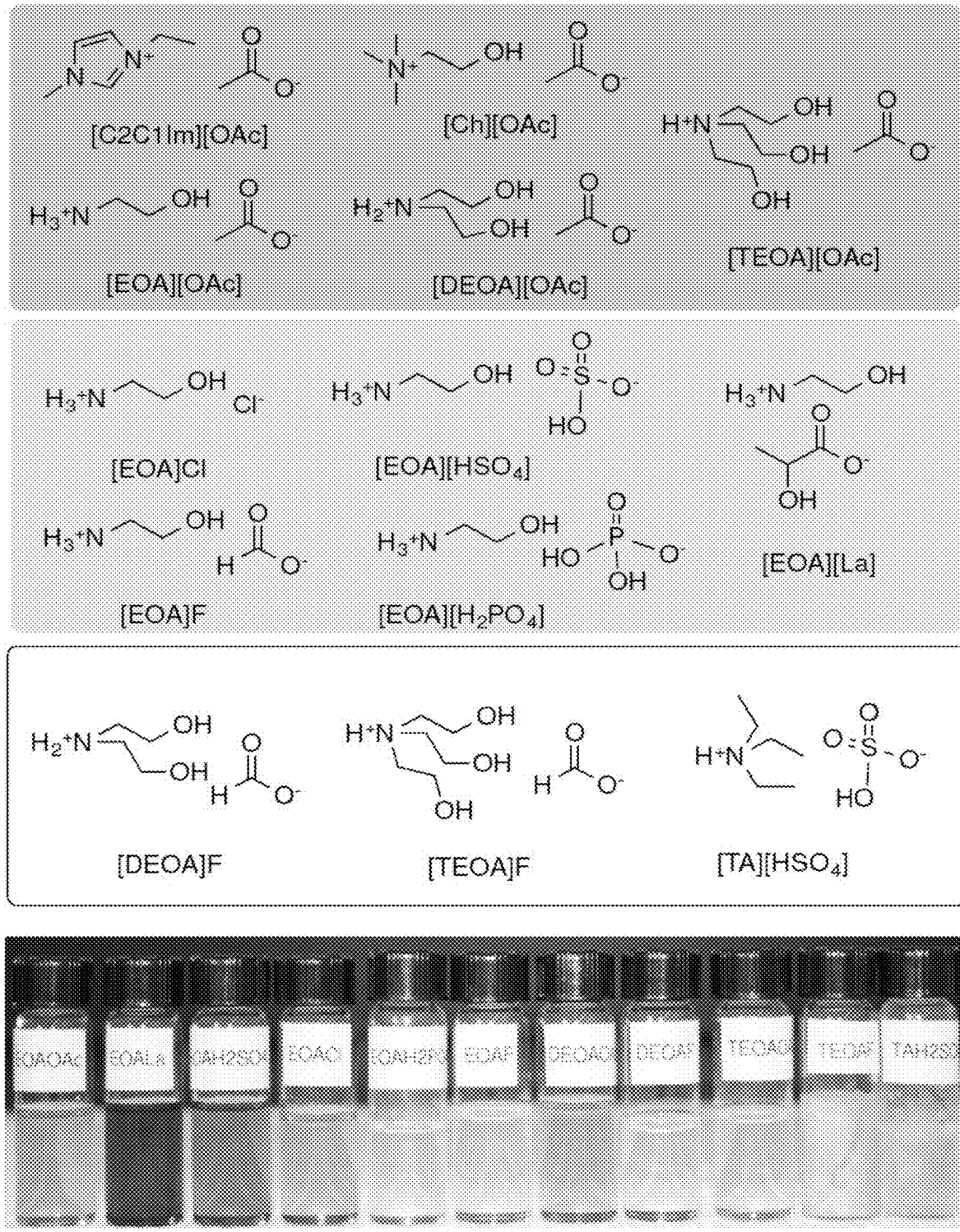
FIG. 2. The chemical structure and picture of ILs synthesized in this work.
Figure 3:
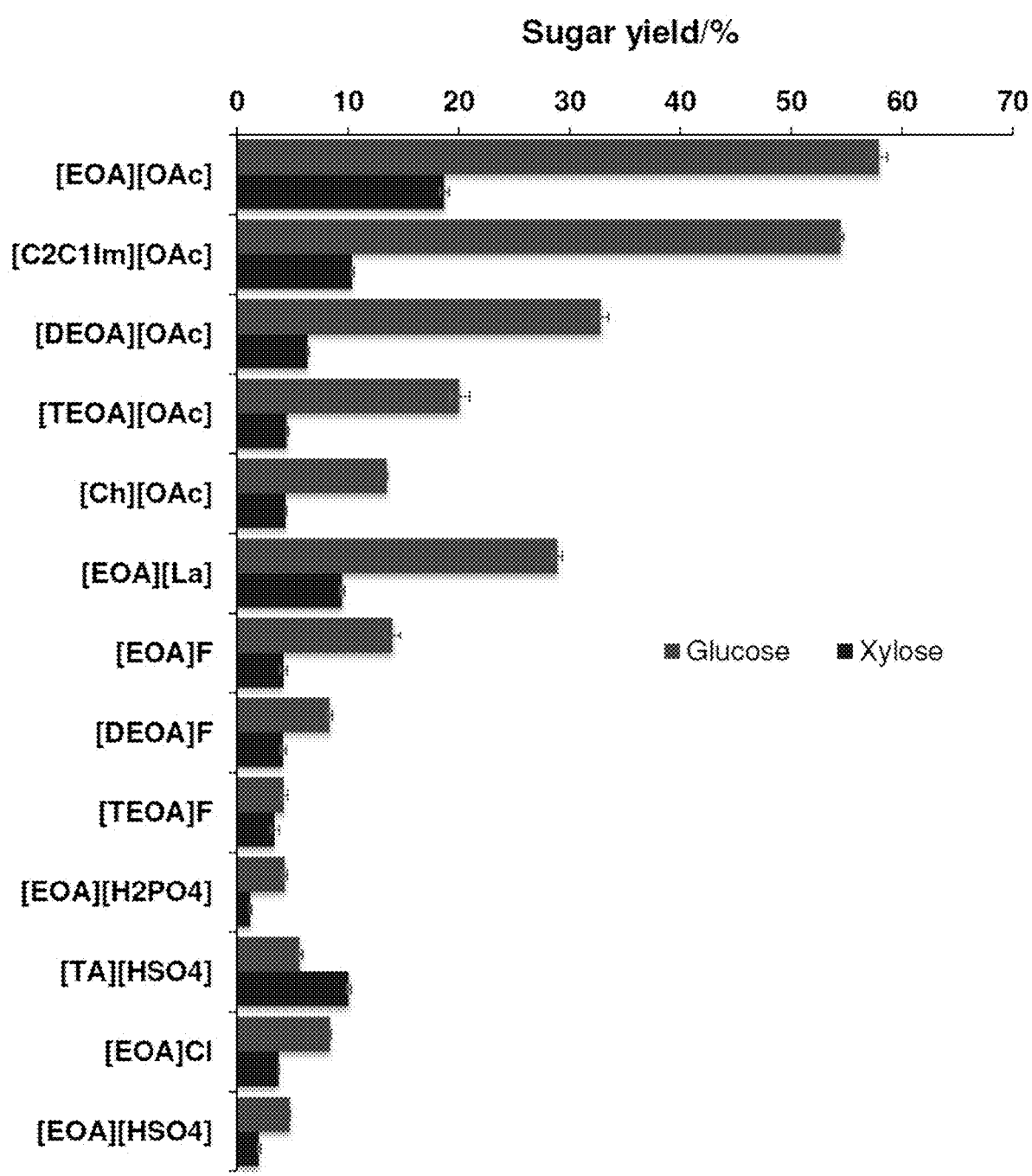
FIG. 3. Effect of IL type on the sugar yield (pretreatment: 10 wt % SG loading, 90 wt % IL, 140° C., 1 h, saccharification: 10 wt % IL, 10 mg protein per g switchgrass, 50° C., 72 h.

In some embodiments, the PIL has the structure of any of the PIL taught herein (such as in FIG. 2 and Table 1).

In some embodiments, the solution has a temperature of about 50° C. to about 160° C. In some embodiments, the solution has a concentration having a value of about 10%, about 20%, about 50%, and about 100%, or any value within a range of concentration of any two of the preceding two percentages.

In some embodiments, the PBIL has the structure [α][β], wherein α is ammonium cation, such as a quaternary amine (such as cholinium), alkylamine (such as ethylamine), or alkanolamine (such as ethanolammonium), or a mixture thereof, and β is phosphate ($PO_4^{3-}$) or hydrogen phosphate ($HPO_4^{2-}$), or a mixture thereof; and the PBIL in the solution has a concentration having a value from about 20% to about 100%. In some embodiments, the PBIL has the structure [α][β], wherein α is cholinium, and β is phosphate ($PO_4^{3-}$) or hydrogen phosphate ($HPO_4^{2-}$), or a mixture thereof; and the PBIL in the solution has a concentration having a value from about 20% to about 100%.

We have developed a method for the efficient pretreatment of lignocellulosic biomass with cholinium and ethanolamine based IL at different pH by tuning anion compositions and in aqueous phase without incorporation of additional steps (further addition of ions or any other external source for pH adjustment). Biocompatiblity and enzyme tolerance can be effectively controlled by these key factors and desired task specific chemistry for resulting products.

We have designed and developed novel ILs based on cholinium [Ch] and ethanolamine [EA] as a cation with variety of anions combinations. For instance, [EA][OAc] IL with pH=4.5 pretreatment showed greater pretreatment efficiency and enzymatic saccharification in terms of nearly 85% glucose yield. We have synthesized [Ch] with [$H_2PO_4$] (pH=4.5), [$HPO_4$] (pH=8, [$PO_4$] (pH=12.5), [HCO3], carboxylic acids and [EA] with [$H_2PO_4$], [OAc], [Formate], [Lysinate] ILs in different pH range from acidic to super basic properties showed task specific performance for lignin removal and glucose yield compared to 1-ethyl-3-methyl-imidazolium acetate ([C2mim][OAc]). Switch grass dissolved in these IL pretreatment showed sugar yield from 60-85%. We have tested the effect of IL on lignin show a notable low molecular weight fragments indicating degradation and catalysis.

We have developed a method for pretreatment of lignocellulosic biomass with cholinium and ethanolamine based IL operates at different pH range by tuning anion compositions. These novel ILs are tested in conventional IL pretreatment and one-pot process and IL in aqueous phase process. Switch grass dissolved in these IL pretreatment showed sugar yield from 60-85% in different IL pH conditions.

We have developed effective pretreatment technology utilizing acidic to basic pH range ILs that are cheap to start without any additional processing and further reduce the pretreatment cost because they perform efficiently in specific pH suitable process conditions for desired product recovery. These ILs are suitable for selective degradation lignin and useful for catalysis.

TABLE 1

Calculated net basicity based screening of cholinium ILs.

| | Net Basicity | Poor (<0.15) | Moderate (0.16-0.25) | Good (0.26-0.5) | Excellent (>0.5) |
|---|---|---|---|---|---|
| Cholinium Formic acid | 0.23 | | | | |
| Cholinium OAc | 0.24 | | + | | |
| Cholinium Chloro OAc | 0.14 | + | | | |
| Cholinium DiCl OAc | 0.17 | | + | | |
| Cholinium TriCl O Ac | 0.07 | + | | | |
| Cholinium Oxalic | 0.08 | + | | | |
| Cholinium Benzoic acid | 0.16 | | + | | |
| Cholinium Malonic acid | 0.18 | | + | | |
| Cholinium Succinic | 0.16 | | + | | |
| Cholinium Glutaric acid | 0.22 | | + | | |
| Cholinium Adipic acid | 0.25 | | + | | |
| Cholinium Pimelic acid | 0.53 | | | | + |
| Cholinium Suberic acid | 0.28 | | | + | |
| Cholinium Azelaic acid | 0.39 | | | + | |
| Cholinium Sebacic acid | 0.59 | | | | + |
| Cholinium citric acid | 0.08 | + | | | |
| Cholinium Propane 23 tricarboxylic acid | 0.17 | | + | | |
| Cholinium Isophthalic acid | 0.17 | | + | | |
| Cholinium ortho Phthalic acid | 0.4 | | | + | |
| Cholinium Terephthalic acid | 0.11 | + | | | |
| Cholinium Maleic acid | 0.34 | | | + | |
| Cholinium mesylate | 0.36 | | | + | |
| Cholinium bitartrate | 0.36 | | | + | |
| Cholinium dihydrogenphosphate | 0.39 | | | + | |
| Cholinium glycolate | 0.3 | | | + | |
| Cholinium lactate | 0.29 | | | + | |
| Cholinium lysinate | 0.27 | | | + | |
| Cholinium Fumaric acid | 0.19 | | + | | |
| Cholinium bicarbonate | 0.16 | | + | | |
| Cholinium lbeta ala | 0.13 | + | | | |
| Cholinium glcinate | −0.01 | + | | | |
| Cholinium Glutamate | −0.05 | + | | | |
| Cholinium Cl | −0.17 | + | | | |
| Cholinium salicylate | −0.28 | + | | | |
| Cholinium 6 amino hexanoic acid | 0.57 | | | | + |

TABLE 2

ILs in different pH.

| | pH | b | a | Net |
|---|---|---|---|---|
| EA-dihydrogenphosphate | 4.5 | 4.17 | 2.626 | 1.55 |
| EA-OAc | 5.5 | 4.02 | 2.515 | 1.5 |
| EA-lysinate-m 1 | 9 | 3.93 | 2.234 | 1.7 |
| Cholinium-H$_2$PO$_4$ | 4.5 | 3.17 | 2.78 | 0.39 |

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

Example 1

One-Pot Integrated Cellulosic Ethanol Production Enabled by Low-Cost Designer Protic Ionic Liquids Moving through the development of biomass conversion process using ionic liquids (ILs), 1-ethyl-3-methylimi-dazolium acetate ([C$_2$C$_1$Im][OAc]), and choline lysinate ([Ch][Lys]) are demonstrated for effective pretreatment of lignocellulosic biomass. However, employing these ILs in an integrated one-pot bioprocessing from biomass to biofuel still challenging due to IL toxicity, significant water-washing requirements, pH compatibility, varying process conditions, and process economics. To address these issues, herein, for the first time, we demonstrated one-pot integrated cellulosic ethanol production enabled by the designer protic ILs (PILs). These PILs comprise inexpensive ions derived from simple amino bases (e.g., ethanolamine, diethanolamine, or triethanolamine, choline) and acids from common commercial sources (e.g., acetic acid, sulfuric acid, phosphoric acid, hydrochloric acid and formic acid). After pretreatment the slurry could be directly used for simultaneous saccharification and fermentation (SSF) in the presence of commercial enzyme and/or wide type yeast without any pH adjustments under water-wash free operations. Outcome of these efforts resulted in 85% glucose and 35% xylose (monomers) are liberated from switchgrass (SG), and a 70% of theoretical ethanol yield is obtained in SSF using as high as 40% SG loading on the pretreatment step. This study opens avenues for an efficient integrated biomass conversion process and more practical solutions to biorefinery.

Lignocellulosic biomass has been recognized as a potential sustainable source of mixed sugars and aromatics for the production of biofuels, chemicals, and other biomaterials.[1,2] However, physicochemical factors such as the crystallinity of cellulose, and cellulose sheathing by hemicellulose and lignin contribute to the recalcitrance of lignocellulose as the major hurdle for its up conversion using chemicals or enzymes.[3] There has been an upsurge of interest in ionic liquids (ILs) based biomass pretreatment due to their unique solvation properties and superior performance compared to other types of pretreatment and process engineering efforts.[4] IL pretreatment process can be varied with different feedstocks, high solid loadings[5], large scale,[6] and/or in continuous mode.[7] The clear objective now is to make IL pretreatment process as cost-competitive and reduce process complexity for today's markets. IL based integrated one-pot of biomass pretreatment, enzymatic hydrolysis and fermentation would be an alternative approach with outstanding potential.

In order to develop integrated IL based biomass conversion, it is necessary to overcome the challenges that have been encountered so far in the IL based processes. Removal of ILs from the pretreated slurry is thought to eliminate its toxicity towards enzymes and microorganisms and produce substrates with appropriate enzymatic digestibility. Unfortunately, the excessive use of water and waste disposal associated with slurry-washing pose an economic challenge for the scale-up of any pretreatment technology.[8] Over the past few years, much effort has been devoted to improve IL biocompatibility,[9,10] and/or develop engineered IL-tolerant enzyme/microbes.[11,12] The other major challenge is the pH compatibility between the three different steps i.e. biomass pretreatment to saccharification to fermentation especially in a case of basic bionic liquids (BILs) used for pretreatment. Basic BILs such as cholinium lysinate, 1-ethyl-3-methyl-imidazolium lysinate, and cholinium acetate, have been investigated because of their excellent pretreatment performances especially with high lignin removal ability.[13] In this context, necessary pH adjustment after pretreatment by mineral acid is generally used, which is seriously impacting IL recovery and regeneration. Despite all of the advantages, IL based biomass conversion efforts currently suffer from the perspectives of its economic feasibilities. Hence, development of biocompatible IL based water wash-free and pH adjustment free one-pot process with commercial enzyme is still highly desirable.

Recently, investigations on the use of hydroxyl ammonium ILs have been carried out for biomass pretreatment. Compared to imidazolium ILs, these class of ILs are less expensive, more easily synthesized, higher biodegradable and biocompatible.[14,15,16,17,18] They have been used in laboratory scale and industrial scale applications including biomass conversion,[13] $CO_2$ absorption/separation/conversion,[16,19,20,21] and $SO_2$ capture/gas desulfurization.[22,23,24,25] However, to the best of our knowledge, no such effort has been carried out on integrated one-pot biomass process using these type of ILs. In this work, for the first time, we evaluated the commercialization potential of low-cost protic ILs (PILs) in an integrated one-pot process for the cellulosic ethanol production. These ILs contains ions derived from simple amino bases (e.g., ethanolamine, diethanolamine, or triethanolamine choline) and acids (e.g., acetic acid, sulfuric acid, phosphoric acid, hydrochloric acid and formic acid). Enabled by higher lignin removal capacity, lower toxicity and matchable pH features of the optimized PIL, the pretreated slurry is directly converted into ethanol via simultaneous saccharification and fermentation (SSF) with commercial enzyme and wide type yeast. As a result, a 70% of theoretical ethanol yield is obtained by using 40% switchgrass (SG) loading on pretreatment. Our results indicate that 85% glucose and 35% xylose (monomers) is liberated from SG for fermentable sugar generation. This one-pot consolidated bioprocessing represents a novel route that: 1) employment of inexpensive, low-toxic and easily-prepared PILs; 2) high biomass loading capacity; 3) water-wash free; 4) no requirement of high-cost IL tolerant enzyme cocktails and engineered microbes; and 5) no need for complicated IL pH adjustment eliminating salt waste.

Results and Discussion

Designing and Screening of ILs

Continued search for an IL with the desirable physical, chemical and biological properties for biomass pretreatment is not viable without the aid of fundamental understanding and predictive development. Solubility is critical property for effective biomass pretreatment for higher sugar yield, either one of the major biomass compounds such as cellulose, lignin, and hemicelluloses needs to be preferentially dissolved by solvents. The inherent intricacy of these biomass compounds associated to the many different types of possible interactions allows very selective dissolution in wide range of different ILs. It has been shown that solvent parameters such as basicity ($\beta$) correlates well with an IL's ability to dissolve lignocellulose,[26,27] and that net basicity correlates with an IL's ability to dissolve cellulose.[27,28]

In protic ionic liquids (PILs), the proton transfer from the acid to the base leads to the presence of proton-donor and proton-acceptor sites, which can be used to build up hydrogen-bond networks.[29] The cations of the investigated PILs are presented in FIG. 2, including simple and inexpensive primary, secondary or tertiary alkylamines such as ethanolamine (EOA), diethanolamine (DEOA), triethanolamine (TEOA), and triethylamine (TEA), while the encountered anions were derived from standard organic and mineral acids such as acetic acid, lactic acid, sulfuric acid, phosphoric acid, formic acid and hydrochloric acid. For comparisons, choline acetate ([Ch][OAc]) and 1-ethyl-3-methyl imidazolium acetate ([$C_2C_1$Im][OAc]) were also investigated.

We calculated molecular acidity, basicity, and net basicity values as well as optimized geometries for these ILs using a set of DFT based global descriptors such as chemical potential ($\mu$) and chemical hardness ($\eta$) from the standard working equations. Table 3 shows IL solvent parameters for ILs investigated here. Comparison of the experimental screening results with the calculated solvent parameters of these ILs shows that effective pretreatment requires an IL with high net basicity. Notably, ethanolamine acetate ([EOA][OAc]) has the highest net $\beta$ values as compared with the other ILs selected for screening. The net basicity values of PILs are considerably higher than [$C_2C_1$Im][OAc] and [Ch][OAc] except ethanolamine chloride ([EOA]Cl), ethanolamine bisulfate ([EOA][$HSO_4$]) and ethylamine bisulfate ([EA][$HSO_4$]). Predictably, more acidic anion counterpart lowering the net basicity values of ILs and an increase in ethyl groups of cations are gradually decreeing the ILs net basicity. From Table 3, it also can be seen that net basicity values of [EOA][OAc], [DEOA][OAc], ethanolamine formate ([EOA]F) and ethanolamine dihydrogen phosphate ([EOA][$H_2PO_4$]) are higher than that of [$C_2C_1$Im][OAc]. In comparison with the —$N(CH_3)_3^+$ group in [Ch][OAc], —$NH_3^+$ group in [EOA] framework tends to have stronger hydrogen bonding interactions with lignocellulosic components, by which enhances biomass solvation.

TABLE 3

Calculated basicity ($\beta$), acidity ($\alpha$), and net basicity values of protic ILs.

| | $\beta$ | $\alpha$ | Net Basicity |
|---|---|---|---|
| [EOA][OAc] | 4.17 | 2.47 | 1.7 |
| [DEOA][OAc] | 4.08 | 2.44 | 1.64 |
| [TEOA][OAc] | 3.64 | 2.73 | 0.91 |
| [EOA]Cl | 3.21 | 2.7 | 0.52 |
| [EOA][$HSO_4$] | 3.56 | 3.1 | 0.46 |
| [EOA][$H_2PO_4$] | 4.17 | 2.63 | 1.55 |
| [EOA][La] | 4.04 | 2.84 | 1.2 |
| [EOA]F | 4.18 | 2.55 | 1.63 |
| [DEOA]F | 4.05 | 2.48 | 1.57 |
| [TEOA]F | 3.68 | 2.82 | 0.86 |
| [TA][$HSO_4$] | 3.63 | 2.68 | 0.95 |
| [$C_2C_1$Im][OAc] | 2.97 | 2.28 | 0.69 |
| [Ch][OAc] | 2.82 | 2.53 | 0.29 |
| [EA][$H_2PO_4$] | 4.35 | 2.79 | 1.56 |
| [EA][OAc] | 4.2 | 2.68 | 1.52 |
| [EA][$HSO_4$] | 3.52 | 3.01 | 0.51 |

The corresponding PILs were synthesized through stoichiometric neutralization reaction of certain acids and bases, and verified by NMR analysis (such as $^1H$ NMR and $^{13}C$ NMR spectrum). The pretreatment performance of PILs on sugar yield was screened at low pretreatment temperature and low enzyme loading. Among all of the PILs, [EOA][OAc] displayed the best performance, and the achieved sugar yields were comparable or even better than [C$_2$C$_1$Im][OAc]. The acetate or formate anion with a variety of cations demonstrated the strong dependence of the performance on the cation. The cations, such as [DEOA], [TEOA] and [TEA], led to lower sugar generations. As previously discussed,[29] the incomplete proton transfer from the acid to the base would result in neutral acid and base species in real PILs, and thus aggregation and association of either ions or neutral species can occur. Primary amine cation appears to have a stronger preference for the formation of A$_n$B aggregates (A=acid, B=base, n>1) than secondary and tertiary amine cations, with free amine present at the 1:1 composition,[29,30] which can contribute to a non-negligible biomass pretreatment efficiency. On the other hand, the anion of PILs also exhibited obvious effect on the sugar yield. Among the anions investigated, acetate was the best one. The PILs derived from strong acids result in low sugar yields. This is possibly because that the proton-transfer process could be improved through the use of stronger acids and/or stronger bases, thus due to much higher acidity of sulfuric acid, hydrochloric acid and formic acid, the corresponding PILs could not provide a suitable pH condition for enzymatic hydrolysis without pH adjustment. Based on the above discussion, [EOA][OAc] was selected for further systematic investigation for the development of integrated one-pot process.

Influence of Parameters on the Produce of Sugars

Figure 4A:
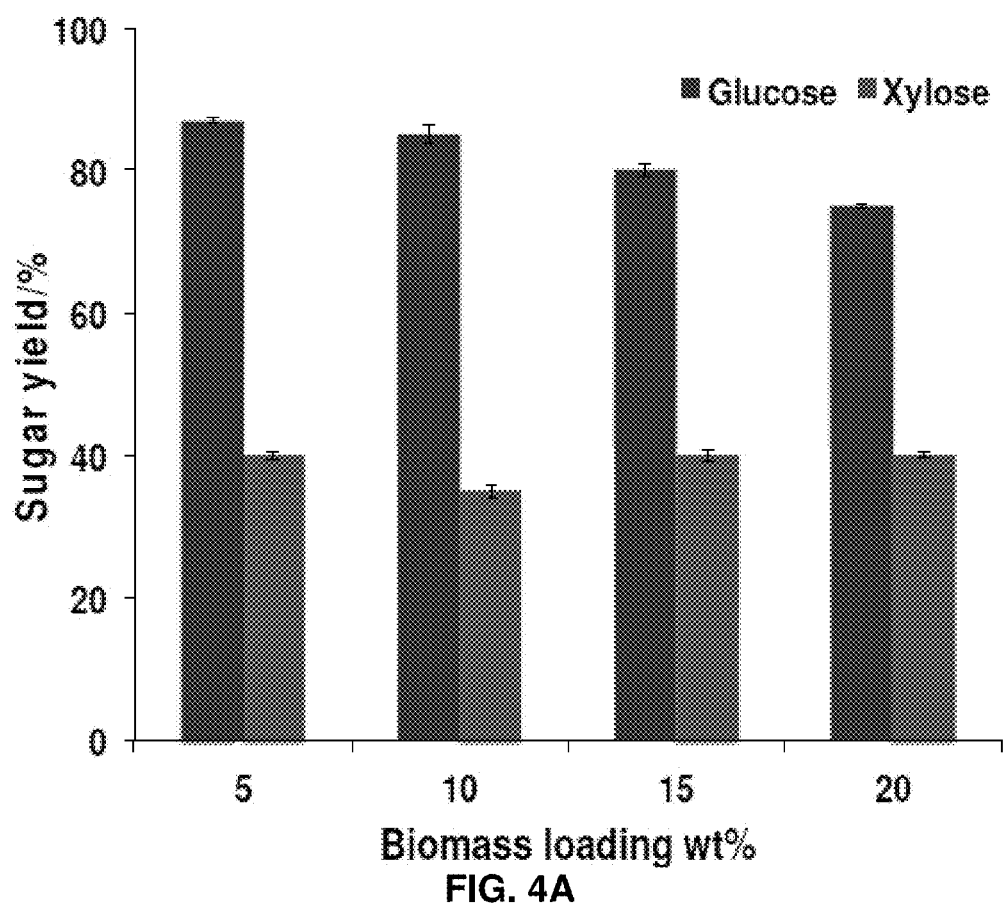
FIG. 4A. Effects of some parameters on the sugar yield: Biomass loading at pretreatment. Normal operation conditions: pretreatment, 10 wt % SG loading, 90 wt % IL, 160° C., 0.5 h (3 h for eucalyptus); saccharification, 10 wt % IL, 20 mg protein/g SG, 50° C., 72 h.

As known, pretreatment conditions (e.g. biomass loading, temperature and time) and saccharification conditions (e.g. IL loading) can greatly affect the reducing sugar production from IL-pretreated biomass, and thus the downstream fermentation will be ultimately affected. Consequently, some key parameter optimization to allow effective saccharification of the whole pretreated SG and potentially reduce the inhibitory factors of enzymes before one-pot integrated ethanol production was conducted. Although the increasing biomass loading at pretreatment step leads to decrease in sugar yield, more than 75% glucose could still be obtained with the biomass loading varying from 5 to 20 wt % (FIG. 4A). Around 60% glucose yield could be achieved at a further increased SG loading of 25 wt % indicating [EOA][OAc] possess an excellent capacity for high loading biomass pretreatment.

Figure 4B:
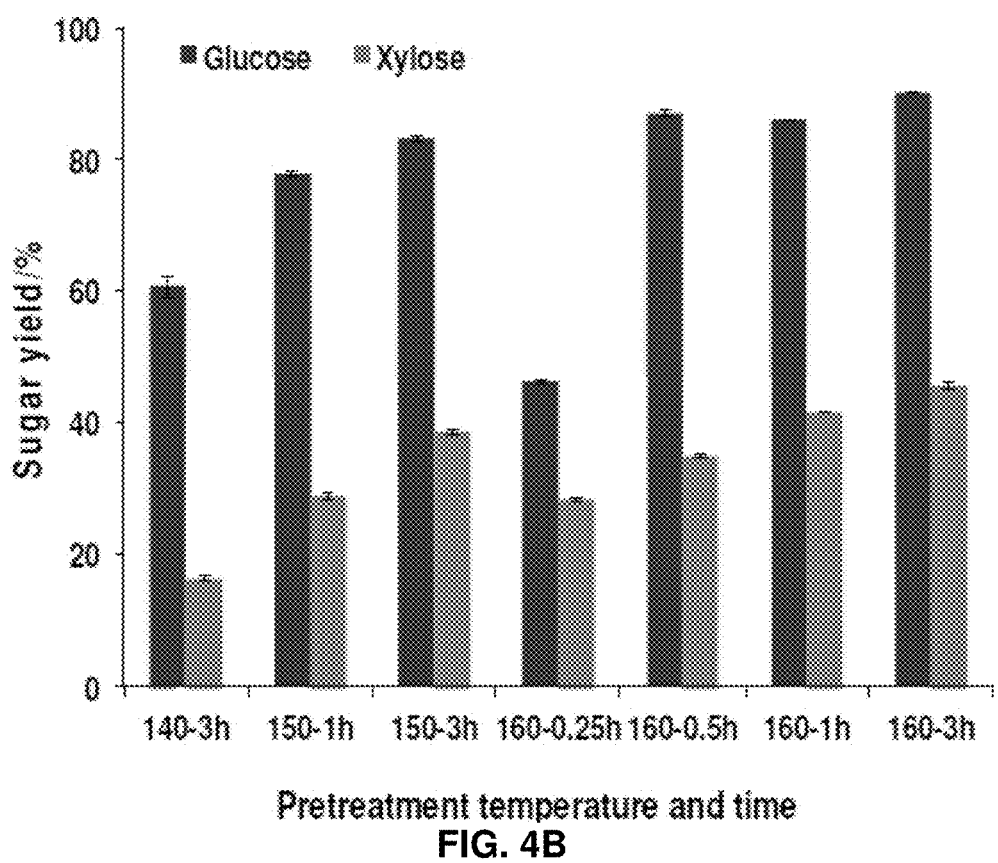
FIG. 4B. Effects of some parameters on the sugar yield: Temperature/time. Normal operation conditions: pretreatment, 10 wt % SG loading, 90 wt % IL, 160° C., 0.5 h (3 h for eucalyptus); saccharification, 10 wt % IL, 20 mg protein/g SG, 50° C., 72 h.

Next, we selected 140° C. as a starting point for the sugar investigation and explored a range of pretreatment conditions from 140 to 160° C. for various time intervals. The resultant sugars appear to be largely affected by the variation in pretreatment temperature. An increase in digestibility of SG from 140 to 160° C. was over 40% (60% vs. 85%) (FIG. 4B). At a 10% SG loading, a satisfactory glucose yield (~85%) could be detected for 160° C. pretreated sample. FIG. 4B also depicted the effect of pretreatment time on the sugar yield. Pretreatment at 160° C. for 15 min could release 45% glucose from SG. Increasing the pretreatment time from 0.5 to 3 hrs slightly increased the yields of glucose and xylose from 85 to 87%, and 35 to 42%, respectively, indicating that the pretreatment time has little effect on the enzymatic saccharification. The study has therefore demonstrated that complete or near complete enzymatic glucan digestion of pretreated SG can be achieved with [EOA][OAc] at a relatively shorter reaction time (30 min) than [C$_2$C$_1$Im][OAc] (3 hrs).[8]

Figure 4C:
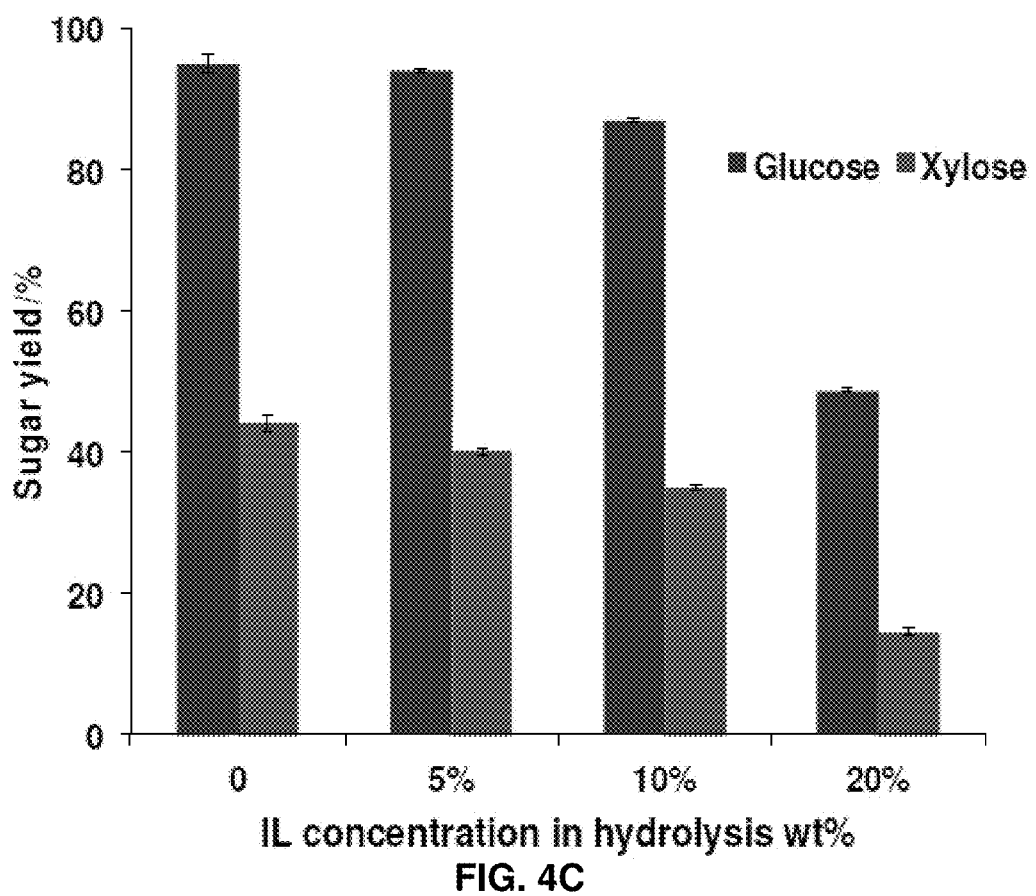
FIG. 4C. Effects of some parameters on the sugar yield: IL concentration in hydrolysis. Normal operation conditions: pretreatment, 10 wt % SG loading, 90 wt % IL, 160° C., 0.5 h (3 h for eucalyptus); saccharification, 10 wt % IL, 20 mg protein/g SG, 50° C., 72 h.

Previous literatures have noted that the ILs based on imidazolium cations, such as 1-n-butyl-3-methylimidazolium chloride ([C$_4$C$_1$Im][Cl]), and [C$_2$C$_1$Im][OAc] are known to deactivate cellulases at fairly low concentrations (~5 wt %).[8,31,32] In the present process, commercial enzyme cocktails, Novozymes Cellic® CTec2 and HTec2 (9:1, v/v), exhibit high levels of tolerance to at least 10 wt % [EOA][OAc] in saccharification process (FIG. 4C). And the corresponding result was competitive to those in 5 and 0 wt % IL loadings. This result implies the potential biocompatibility of [EOA][OAc].

Figure 4D:
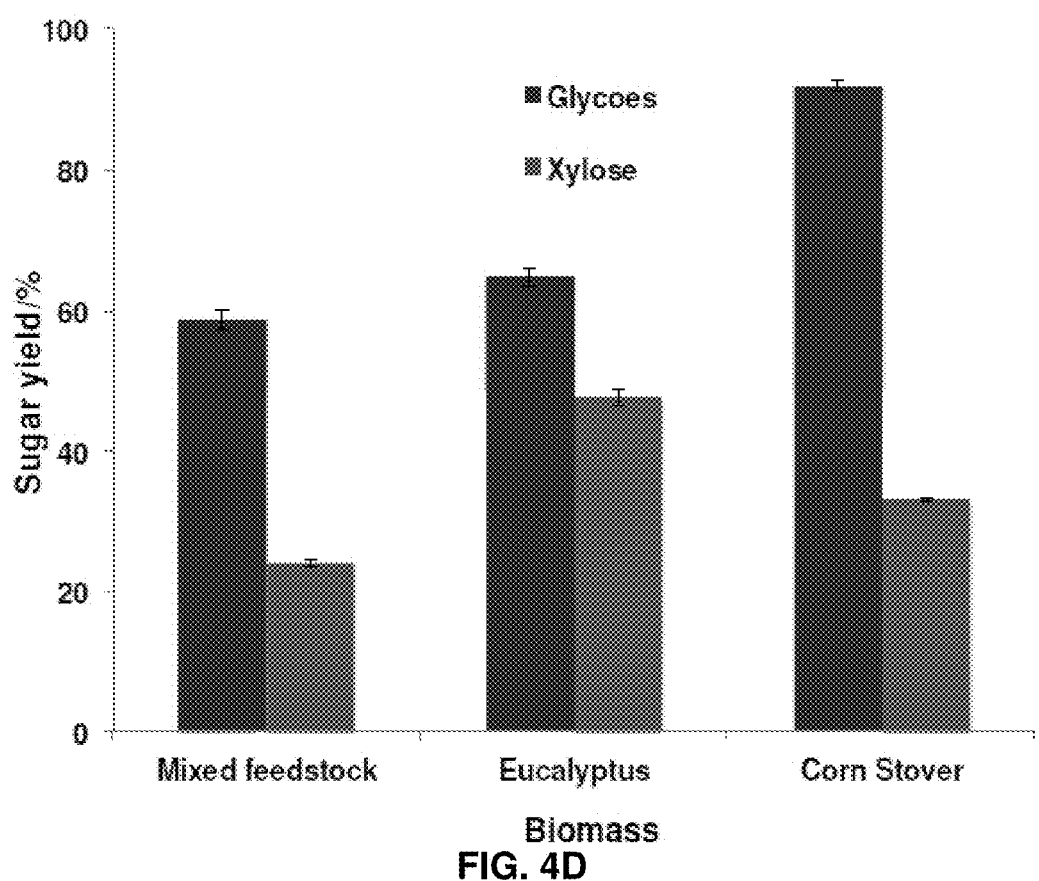
FIG. 4D. Effects of some parameters on the sugar yield: Biomass category. Normal operation conditions: pretreatment, 10 wt % SG loading, 90 wt % IL, 160° C., 0.5 h (3 h for eucalyptus); saccharification, 10 wt % IL, 20 mg protein/g SG, 50° C., 72 h.

Thereafter, we explored the feasibilities of [EOA][OAc] for the pretreatment of different feedstocks including mixed feedstocks of SG and *eucalyptus* (1:1, w/w), *eucalyptus* (EU), and corn stover (CS). It could be seen from FIG. 4D that among of the biomass investigated, [EOA][OAc] displayed the best performance on CS, and the achieved sugar yields are comparable to SG. The low sugar yields in the cases of mixed feedstocks and EU are likely caused by the high lignin content in the corresponding biomass.

Compositional Analysis and X-Ray Diffraction Studies of Untreated and Pretreated Switchgrass Based on the aforementioned discussion, it was found that the pretreatment temperature played a significant effect on the sugar yield. As reported by many literatures, in pretreatment step, the capacities of ILs exhibit for dissolving cellulose and delignification are key factors to realize high pretreatment efficiency. Thus, compositional analysis of untreated, and pretreated SG with [EOA][OAc] at different temperatures and time was studied and the results were summarized in Table 4. Solid recovery refers to the mass percentage of biomass (dry weight) recovered from the original biomass load. After washing, 55-81% of the biomass was recovered. Generally, pretreatment under higher temperature conditions resulted in less solid recovery.[13] Three of the major plant cell wall components of SG, such as glucan, xylan, and acid insoluble lignin were monitored before and after pretreatment. Untreated SG contained 29.6% glucan, 18.4% xylan and 20% acid insoluble lignin (entry 1). After pretreatment, the glucan loading generally increased and higher temperature or longer time resulted in higher glucan contents in pretreated biomass. However, this trend is inconspicuous when the temperature was reach up to 160° C., where the glucan contents were similar after SG was treated for 0.5, 1 and 3 hrs (48.0 vs. 48.9 and 49.8%, respectively) (entries 6-8). However, xylan contents for pretreated biomass were not increased too much compared to those of the original biomass, varying within a range of around 24-27%. On the other hand, lignin content of pretreated material generally decreased as compared to the original biomass. This trend was most obvious after pretreatment under higher temperature where lignin content was reduced by 77% (untreated: 20% vs. pretreated: 4.7%). The removal or recovery of major components was calculated based on the method described in our previous work.[13] Although the compositional changes do not always reflect the actual component recovery because of the different solid recovery, higher temperature IL pretreatment facilitated lignin removal. These results obtained with [EOA][OAc] IL are consistent with our previous report by using basic ILs such as [Ch][Lys] and [C$_2$C$_1$Im][Lys].[13]

TABLE 4

Compositional analysis of swithcgrass after [EOA][OAc] pretreatment.[a]

| T/t (° C./h) | Solid recovery/% | Glucan/% | Xylan/% | Lignin/% |
|---|---|---|---|---|
| —/— | — | 29.6 ± 0.1 | 18.4 ± 0.1 | 20.0 ± 0.1 |
| 120/1 | 80.67 | 40.6 ± 0.4 | 25.4 ± 0.2 | 11.6 ± 0.5 |
| 120/3 | 75.60 | 42.5 ± 0.7 | 26.0 ± 0.1 | 9.1 ± 1.8 |
| 140/1 | 65.03 | 48.2 ± 0.6 | 24.2 ± 1.1 | 8.4 ± 1.2 |
| 140/3 | 63.57 | 47.5 ± 0.1 | 24.0 ± 0.4 | 6.5 ± 0.4 |
| 160/0.5 | 56.17 | 48.0 ± 1.6 | 25.8 ± 0.6 | 6.1 ± 1.4 |
| 160/1 | 55.77 | 48.9 ± 1.6 | 26.6 ± 0.5 | 5.7 ± 1.6 |
| 160/3 | 55.37 | 49.8 ± 0.2 | 26.1 ± 0.9 | 4.7 ± 0.8 |

[a]Solid loading 10 wt %.

The proportions of crystalline/amorphous cellulose and the disordered components (i.e. amorphous cellulose, hemicelluloses and lignin) found in pretreated SG samples were determined by pXRD. The diffraction patterns of untreated SG and treated SG with 5 and 10 wt % biomass loading shows three similar peaks are observed in the diffraction patterns for all of the samples: the main peak position at 21.7° is indicative of the distance between hydrogen-bonded sheets in cellulose I; the broad peak at ~16° is known to be a composite of two peaks from $I_\beta$, $I_\alpha$, or both;[33] and the third small peak at 34.5° corresponds to ¼ of the length of one cellobiose unit and arises from ordering along the fiber direction.[34] Although SG pretreated by [EOA][OAc] still retains primarily a cellulose I structure same with raw feedstock, small shift in the three peaks can be attributed to the removal of amorphous lignin, which is also consistent with the result in Table 4. To further understand cellulose structural changes during pretreatment with [EOA][OAc], Avicel was pretreated under the same conditions and the XRD spectra is also plotted. After pretreating Avicel in [EOA][OAc], although cellulose I structure is still dominated as displayed in XRD patterns, the characteristic diffraction peak positions are little different from untreated Avicel (i.e. cellulose I and amorphous). It has been shown that anions of ILs play a critical role in cellulose solubilization, and those that accept hydrogen bonds from cellulose hydroxyl protons can effectively disrupt the inter- and intramolecular hydrogen bonding in cellulose.[35] However, the acetate anion with different cations demonstrated the strong dependence of the performance on the cation. The replacement of [$C_2C_1$Im] by [EOA] cation lead to a negligible effect on the crystalline structure change of cellulose, which is possibly due to the stronger inter-hydrogen bonds in the PIL than the intra-hydrogen bonds between PIL and cellulose.

One-Pot Integrated Cellulosic Ethanol Production

Simultaneous saccharification and fermentation (SSF) after pretreatment is a frequent practice for cellulosic ethanol production recently. The presence of yeast together with the cellulolytic enzyme cocktail reduces the accumulation of sugars-therefore increasing yield and saccharification rate compared with separate saccharification and fermentation.[36] Our previous studies have demonstrated successful high ethanol production from cellulosic biomass using SSF in the presence of basic IL.[37] However, pH adjustment is still a requirement for that case due to the basicity of IL, by which a difficult IL generation is still a challenge.

Generally, SSF requires compatible fermentation and saccharification conditions, with a similar pH, temperature and optimum substrate concentration. In a case of IL participating SSF, a compromise IL concentration for the two stages is an accessional requirement. Based on the result in FIG. 4C, it was concluded that commercial enzyme cocktails can tolerant a 10 wt % of [EOA][OAc]. However, it is still necessary to further identify the IL concentration that enables fermentation using wild type strains.

Figure 5A:
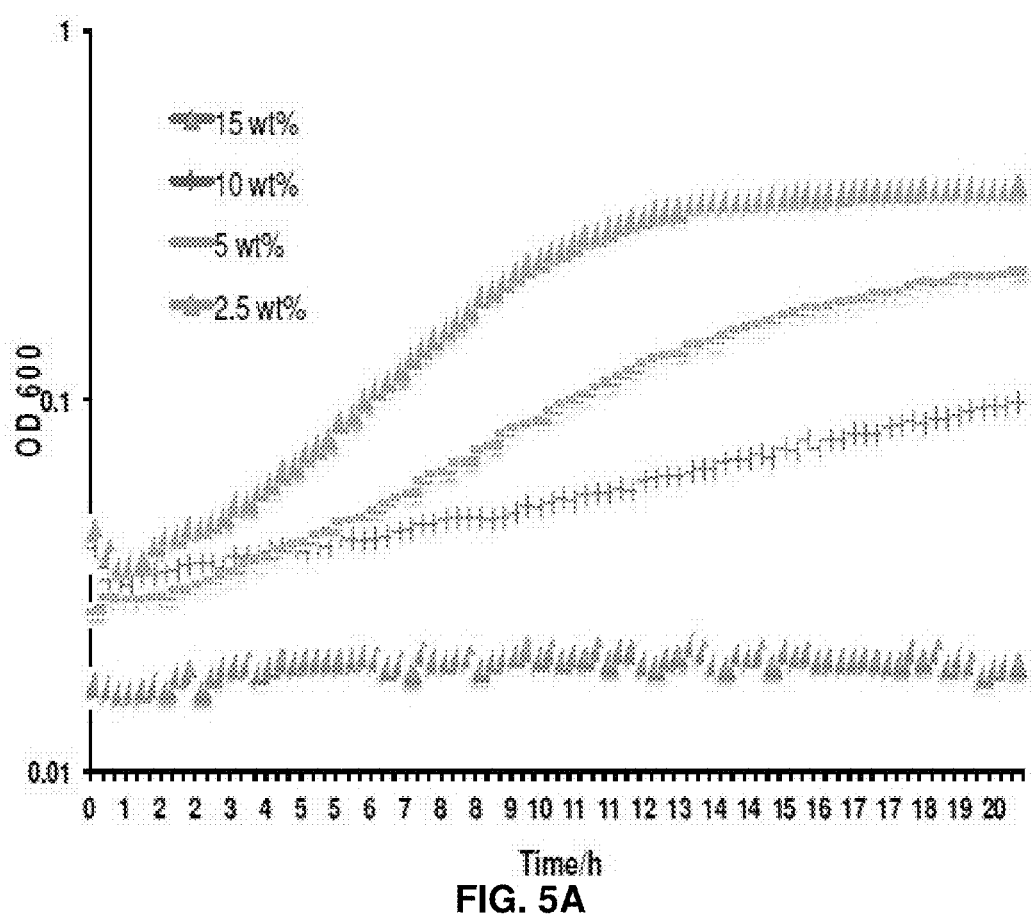
FIG. 5A. Toxicity test of [EOA][OAc] (A) and effect of biomass loading on sugar yield (B). Conditions: yeast strain: *Saccharomyces cerevisiae* strain BY4741, growth condition: in 24-well microplate with orbital-high intensity shaking/31° C./in IL solution (10 g/L glucose in each IL solutions), volume of the cell culture was 0.5 mL.

For toxicity screening, a wild type S. cerevisiae BY4741 strain was technically used and it was immersed in various IL concentrations from 2.5 to 15 wt %. As shown in FIG. 5A, the IL concentration plays a significant effect on the yeast strain growth. A better growth occurs in a lower IL titer below 10 wt %. Since 5 wt % IL concentration could guarantee a better yeast growth, it was chosen during the present SSF.

Figure 5B:
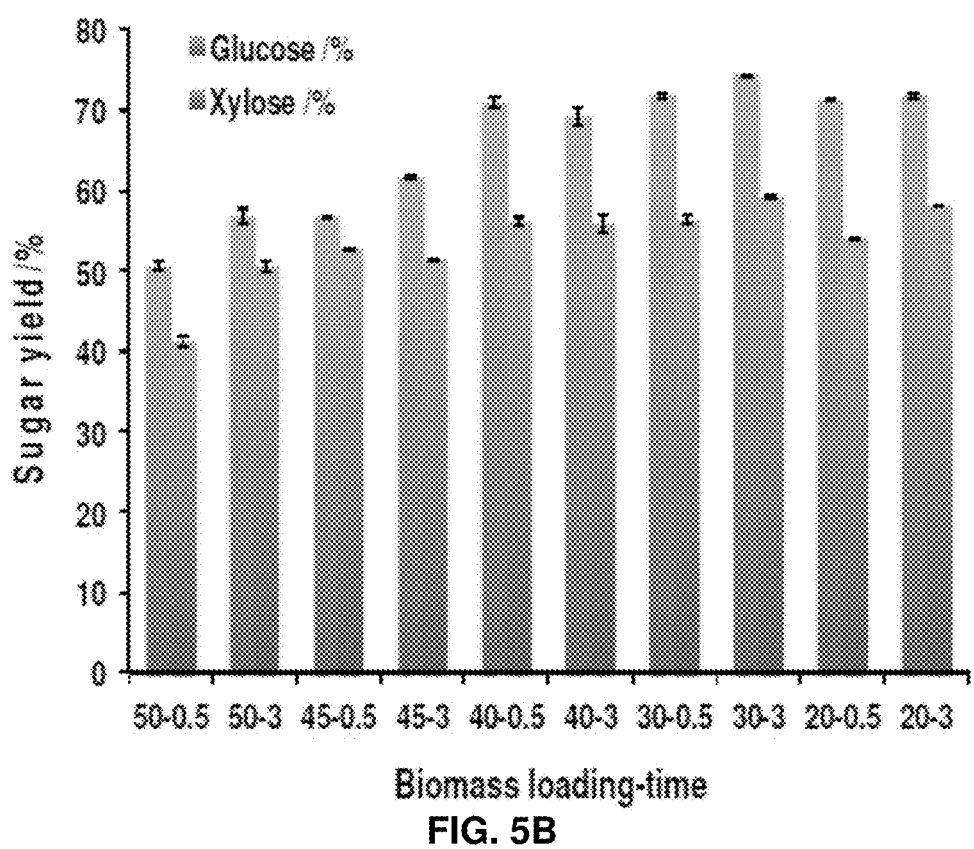
FIG. 5B. Toxicity test of [EOA][OAc] (A) and effect of biomass loading on sugar yield (B). Conditions: pretreatment, x wt % SG loading, (100−x) wt % IL, 160° C., 0.5 h; saccharification, 5 wt % IL, 20 mg protein/g SG, 50° C., 72 h.

FIG. 5B shows that 40 wt % starting biomass loading (i.e. 60 wt % IL) in pretreatment and then was diluted to a 5 wt % IL concentration in saccharification could generate a comparative glucose yield with 20 wt % starting biomass loading, which is favorite to a high capacity of biomass pretreatment based SSF process. Based on this result, 40 wt % starting biomass loading are therefore advisable when employing coupled SSF processes. Other conditions such as temperature and time as well as operation procedure were obtained from our previous work.

Figure 6A:
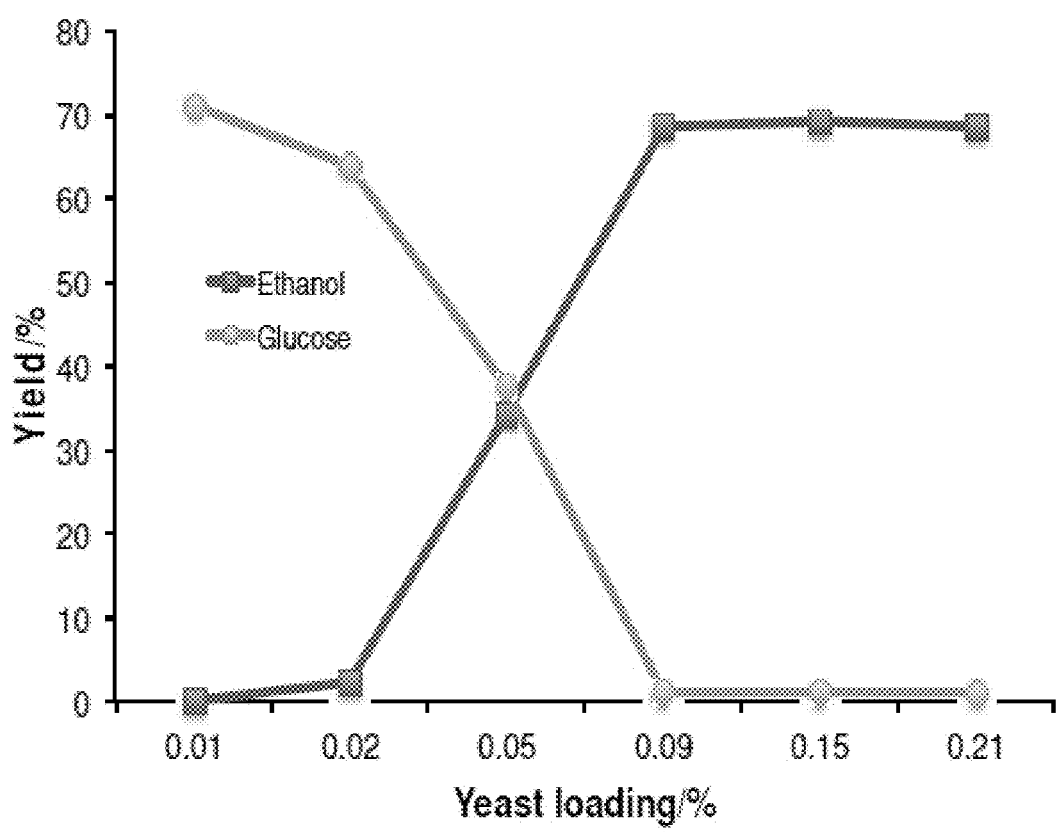
FIG. 6A. Process optimization of one-pot ethanol fermentation after [EOA][OAc] pretreatment. Effect of yeast loading on ethanol fermentation. Conditions: pretreatment, 40 wt % SG loading, 60 wt % IL, 160° C., 0.5 h; saccharification, 5 wt % IL, 20 mg protein/g SG, pH 5, 50° C., 24 h; fermentation, 37° C., 72 h.
Figure 6B:
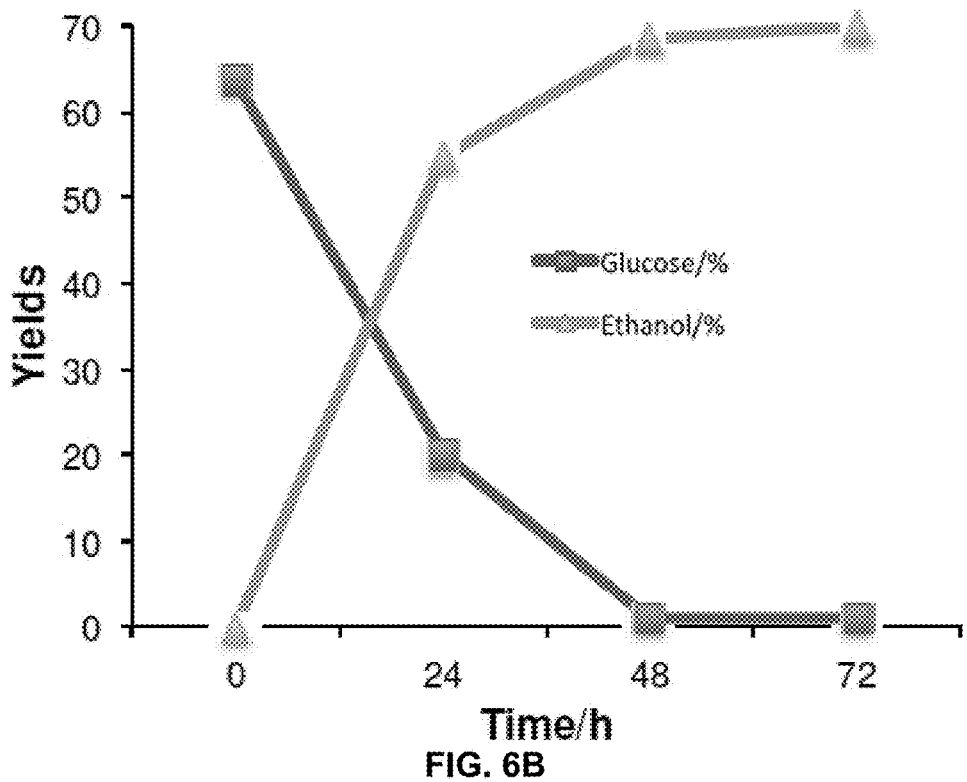
FIG. 6B. Process optimization of one-pot ethanol fermentation after [EOA][OAc] pretreatment. Illustration of the glucose consumption and ethanol production during SSF. Conditions: pretreatment, 40 wt % SG loading, 60 wt % IL, 160° C., 0.5 h; saccharification, 5 wt % IL, 20 mg protein/g SG, pH 5, 50° C., 24 h; fermentation, 37° C., 72 h.

Based on the above results, performance of yeast in SSF was then investigated with different yeast inoculation varying from 0.01 to 0.5 wt %. FIG. 6A suggests that there is no significant difference in ethanol yield when the yeast loading increased from 0.01 to 0.21 wt %. At pretty low yeast loading of 0.1 wt %, that is 1 g/L, around 70% of theoretical ethanol yield could be obtained. The weight ratio of biomass feeding amount to yeast is as high as around 33.3:1 indicating that the one-pot process developed in this work could be more efficient with high biomass loading. FIG. 6B shows the dynamics of sugar consumption and ethanol production with the time under these conditions. After two days, the ethanol yield almost reaches the top value.

Figure 7:
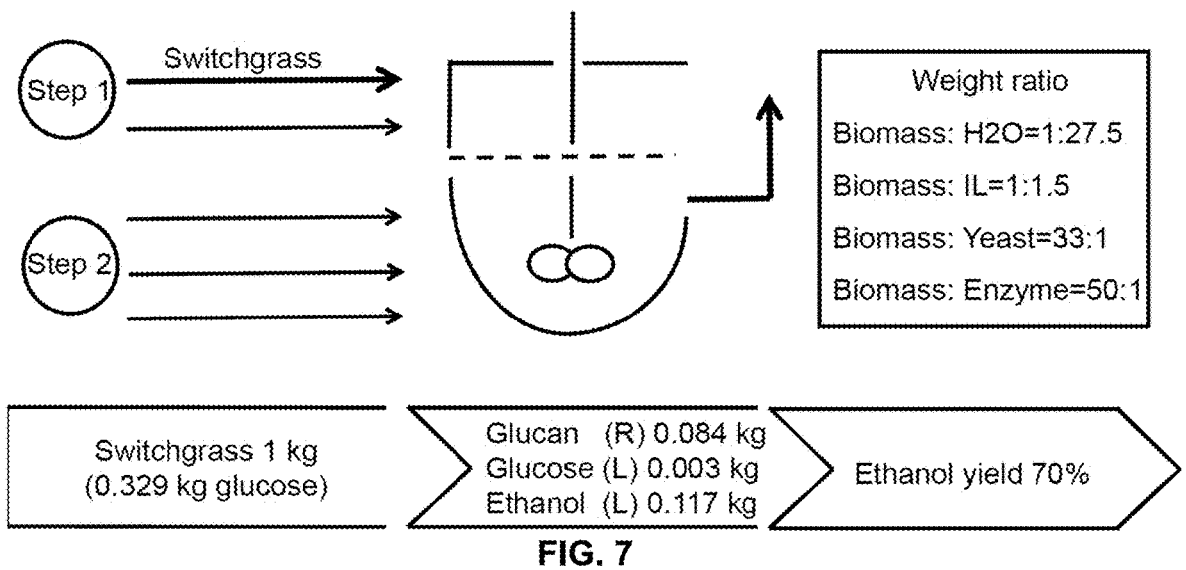
FIG. 7. Illustration of the glucose consumption and ethanol production during SSF. Conditions: pretreatment, 40 wt % SG loading, 60 wt % IL, 160° C., 0.5 h; saccharification, 5 wt % IL, 20 mg protein/g SG, 50° C., 24 h; fermentation, 37° C., 72 h.
Figure 8:
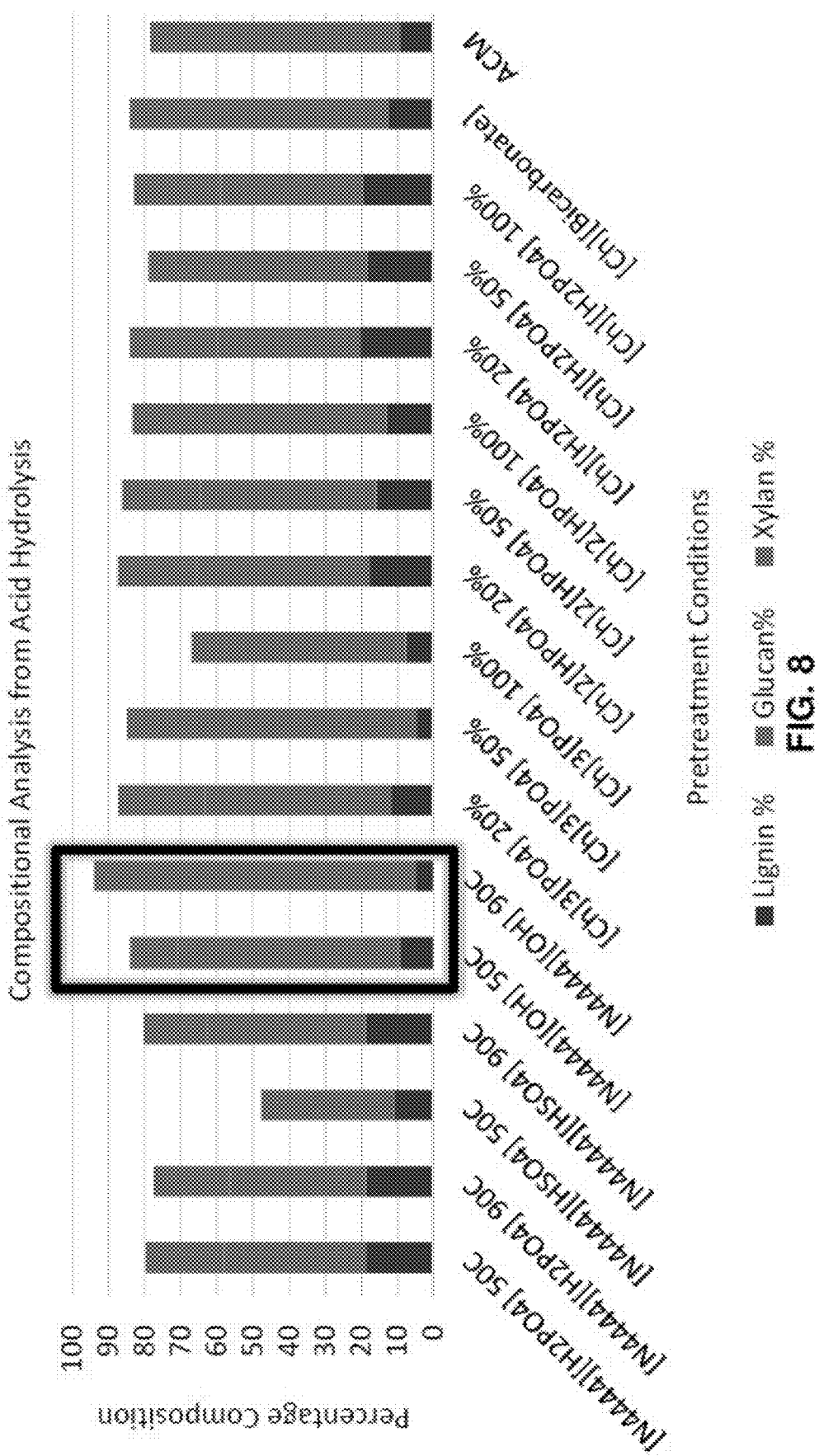
FIG. 8. Composition Analysis.
Figure 9:
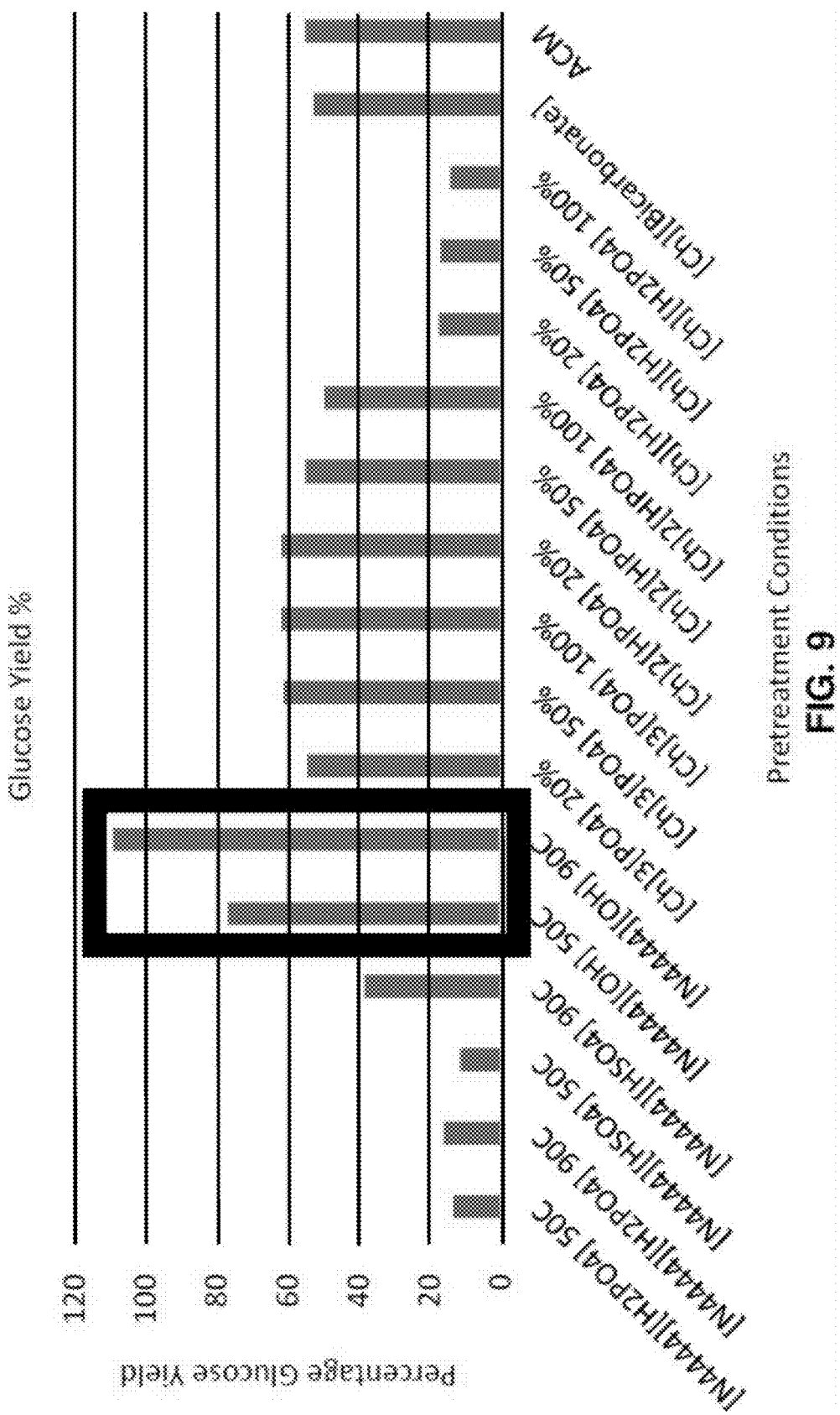
FIG. 9. Glucose yield from enzymatic saccharification.

FIG. 7 described the glucan balances for the [EOA][OAc] based integrated one-pot process. By increasing the biomass loading, the one-pot process results in minimized IL usage as low as 1.5 kg/kg of biomass. In addition, this process realizes yeast loading as low as 0.03 kg/kg of biomass. The glucan/glucose balance suggests over 90% of glucose from saccharification has been converted to ethanol, yielding an overall conversion of 70% in one-pot. As a result, 117 g ethanol was produced from the glucan present in 1 kg of SG. In the future, the utilization the xylose in the hydrolysates could generate a more cost efficient process. For example, a microorganism that is capable of converting both glucose and xylose could utilize this concentrated sugar stream for improved biofuel yield.

CONCLUSIONS

Herein, one-pot integrated process for the producing of cellulosic ethanol is demonstrated for the first time enabled by low-cost, biocompatible protic ionic liquid (PIL). The PIL, ethanolamine acetate [EOA][OAc], contains ions derived from cheap and commercially available compounds of ethanolamine and acetic acid. More importantly, commercial enzyme cocktails and wild type yeast strain are utilized without pH adjustment and water-washing operation throughout the process. Under optimized conditions, a 70% of theoretical ethanol yield could be achieved using 40 wt % swichgrass loading at pretreatment step. In addition, 85% glucose and 35% xylose (monomers) are liberated from switchgrass after a short time pretreatment. The high delignification effect of [EOA][OAc] is the key reason for its high pretreatment efficiency. This current process establishes a new approach to affordable and scalable biomass conversion using efficient, and low cost IL under pH adjustment free and water washing free conditions. It is anticipated that there will be strong growth in the field of PILs as they become more widely known, which will lead to their use in many more applications.

EXPERIMENTAL SECTION

Materials

Switchgrass (SG) (*Panicum virgatum*) was provided by Dr. Daniel Putnam, University of California at Davis. Switchgrass was ground by a Wiley Mill through a 2 mm screen and separated by a vibratory sieve system (Endecotts, Ponte Vedra, FL). The SG fractions falling between 20 and 40 mesh were collected for use in this study and without drying. The SG contains 29.6%±0.01 glucan, 18.4%±0.01 xylan, 20.0%±0.01 lignin, 8.1%±0.01 $H_2O$ and 23.9% of other compounds remaining unidentified, on original basis. Microcrystalline cellulose (MCC, trademark name: Avicel) was purchased from Sigma-Aldrich (St. Louis, MO). The commercial enzyme products cellulase (Cellic® CTec2, Batch#VCN10001) and hemicellulase (Cellic® HTec2, Batch#VHN00001) were gifts from Novozymes, North America (Franklinton, NC).

Compositional Analysis

Compositional analysis of SG before and after pretreatment was performed using NREL acidolysis protocols (LAP) LAP-002 and LAP-005, which was described in our previous work.[13] In a typical process, 200 mg of biomass and 2 mL of 72 wt % $H_2SO_4$ were incubated at 30° C. while shaking at 300 rpm for 1 h. The solution was diluted to 4 wt % $H_2SO_4$ with 56 mL of DI water and autoclaved for 1 h at 121° C. The reaction was quenched into an ice bath before removing the biomass by filtration. Carbohydrate concentrations were determined from the filtrate using an Agilent HPLC 1200 Series equipped with a Bio-Rad Aminex HPX-87H column and a Refractive Index detector. An aqueous solution of $H_2SO_4$ (4 mM) was used as the mobile phase (0.6 mL min$^{-1}$, column temperature 50° C.). The injection volume was 20 pt with a run time of 20 min. Acid insoluble lignin was quantified gravimetrically from the solid after heating overnight at 105° C. (the weight of acid-insoluble lignin+ash) and then at 575° C. for at least 6 h (the weight of ash).

One-Pot Pretreatment and Saccharification

In a typical procedure, SG (100 mg) was mixed with ([EOA][OAc]) at a 10% biomass loading in a 15 mL capped glass pressure tube and pretreated in a convection oven at 160° C. for 0.5 h. Untreated raw SG (30-40 mesh) was used as a control. After pretreatment, the pretreated slurry was diluted with water to obtain a final IL concentration of 10 wt %. Enzymatic saccharification step was operated at 50° C. for 72 hrs with constant agitation on an Enviro Genie SI-1200 rotator platform (Scientific Industries, Inc., Bohemia, NY). The loading of enzyme cocktails (9CTec2/HTec2, v/v) is 20 mg EP per g SG.

One-Pot Pretreatment and SSF

In a typical procedure, SG (100 mg) was mixed with ([EOA][OAc]) at a 40% biomass loading in a 15 mL capped glass pressure tube and pretreated in a convection oven at 160° C. for 0.5 h. After pretreatment, the pretreated slurry was diluted with DI-water to obtain a final IL concentration of 5 wt %, and pre-saccharificated for 24 h under the same aforementioned conditions. Simultaneously, wide type yeast strain BY4741 was prepared. After the addition of yeast strain, the SSF step was conducted for 72 hrs.

X-Ray Diffraction (XRD) and NMR Spectroscopy

The raw and pretreated biomass were dried and characterized with powder X-ray diffraction (PXRD). The XRD analysis were performed on a PANalytical Empyrean X-ray diffactometer equipped with a PIXcel$^{3D}$ detector and operated at 45 kV and 40 kA using Cu Kα radiation (λ=1.5418 Å). The patterns are collected in the 2θ range from 5 to 60° with a step size of 0.039° and the exposure time of 300 seconds. A reflection-transmission spinner was used as a sample holder and the spinning rate was set at 8 rpm throughout the experiment.

NMR spectra were acquired at 298 K using a Bruker Avance-600 MHz instrument in DMSO-d6 and calibrated with the corresponding DMSO peak (δH=2.50 ppm for $^1H$ and δC=39.50 ppm for $^{13}C$).

REFERENCES CITED

1 H. Wang, G. Gurau and R. D. Rogers, *Chemical Society Reviews*, 2012, 41, 1519.

2 M. E. Himmel, S. Y. Ding, D. K. Johnson, W. S. Adney, M. R. Nimlos, J. W. Brady and T. D. Foust, *Science*, 2007, 315, 804.

3 N. Mosier, C. Wyman, B. Dale, R. Elander, Y. Y. Lee, M. Holtzapple and M. Ladisch, *Bioresource Technol*, 2005, 96, 673.

4 J. P. Hallett and T. Welton, *Chemical Reviews*, 2011, 111, 3508.

5 J. Shi, V. S. Thompson, N. A. Yancey, V. Stavila, B. A. Simmons and S. Singh, *Biofuels*, 2013, 4, 63.

6 C. L. Li, D. Tanjore, W. He, J. Wong, J. L. Gardner, K. L. Sale, B. A. Simmons and S. Singh, *Biotechnology for Biofuels*, 2013, 6.

7 A. S. A. da Silva, R. S. S. Teixeira, T. Endo, E. P. S. Bon and S.-H. Lee, *Green Chemistry*, 2013, 15, 1991.

8 J. Shi, J. M. Gladden, N. Sathitsuksanoh, P. Kambam, L. Sandoval, D. Mitra, S. Zhang, A. George, S. W. Singer, B. A. Simmons and S. Singh, *Green Chem*, 2013, 15, 2579.

9 G. Quijano, A. Couvert and A. Amrane, *Bioresource Technol*, 2010, 101, 8923.

10 S. K. Tang, G. A. Baker and H. Zhao, *Chemical Society Reviews*, 2012, 41, 4030.

11 J. I. Park, E. J. Steen, H. Burd, S. S. Evans, A. M. Redding-Johnson, T. Batth, P. I. Benke, P. D'haeseleer, N. Sun, K. L. Sale, J. D. Keasling, T. S. Lee, C. J. Petzold, A. Mukhopadhyay, S. W. Singer, B. A. Simmons and J. M. Gladden, *Plos One*, 2012, 7.

12 J. M. Gladden, J. I. Park, J. Bergmann, V. Reyes-Ortiz, P. D'haeseleer, B. F. Quirino, K. L. Sale, B. A. Simmons and S. W. Singer, *Biotechnol Biofuels*, 2014, 7.

13 N. Sun, R. Parthasarathi, A. M. Socha, J. Shi, S. Zhang, V. Stavila, K. L. Sale, B. A. Simmons and S. Singh, *Green Chem*, 2014, 16, 2546.

14 L. Chen, M. Sharifzadeh, N. Mac Dowell, T. Welton, N. Shah and J. P. Hallett, *Green Chem*, 2014, 16, 3098.

15 K. Ohira, Y. Abe, M. Kawatsura, K. Suzuki, M. Mizuno, Y. Amano and T. Itoh, *ChemSusChem*, 2012, 5, 388.

16 L. C. Tomé, D. J. S. Patinha, R. Ferreira, H. Garcia, C. Silva Pereira, C. S. R. Freire, L. P. N. Rebelo and I. M. Marrucho, *ChemSusChem*, 2014, 7, 110.

17 Q.-P. Liu, X.-D. Hou, N. Li and M.-H. Zong, *Green Chem*, 2012, 14, 304.
18 Y. Fukaya, Y. Iizuka, K. Sekikawa and H. Ohno, *Green Chem*, 2007, 9, 1155.
19 X. L. Yuan, S. J. Zhang and X. M. Lu, *Journal of Chemical & Engineering Data*, 2007, 52, 596.
20 X. Yuan, S. Zhang, J. Liu and X. Lu, *Fluid Phase Equilibria*, 2007, 257, 195.
21 J. Sun, S. Zhang, W. Cheng and J. Ren, *Tetrahedron Letters*, 2008, 49, 3588.
22 L. Zhai, Q. Zhong, C. He and J. Wang, *Journal of Hazardous Materials*, 2010, 177, 807.
23 B. Guo, E. Duan, A. Ren, Y. Wang and H. Liu, *Journal of Chemical & Engineering Data*, 2009, 55, 1398.
24 G. Cui, C. Wang, J. Zheng, Y. Guo, X. Luo and H. Li, *Chemical Communications*, 2012, 48, 2633.
25 M. Ismail Hossain, M. El-Harbawi, Y. A. Noaman, M. A. B. Bustam, N. B. M. Alitheen, N. A. Affandi, G. Hefter and C.-Y. Yin, *Chemosphere*, 2011, 84, 101.
26 A. Brandt, J. P. Hallett, D. J. Leak, R. J. Murphy and T. Welton, *Green Chem*, 2010, 12, 672.
27 A. Parviainen, A. W. T. King, I. Mutikainen, M. Hummel, C. Selg, L. K. J. Hauru, H. Sixta and I. Kilpelainen, *Chemsuschem*, 2013, 6, 2161.
28 L. K. J. Hauru, M. Hummel, A. W. T. King, I. Kilpeläinen and H. Sixta, *Biomacromolecules*, 2012, 13, 2896.
29 T. L. Greaves and C. J. Drummond, *Chemical Reviews*, 2008, 108, 206.
30 C. F. Poole, *J Chromatogr A*, 2004, 1037, 49.
31 J. M. Gladden, M. Allgaier, C. S. Miller, T. C. Hazen, J. S. VanderGheynst, P. Hugenholtz, B. A. Simmons and S. W. Singer, *Appl Environ Microb*, 2011, 77, 5804.
32 M. B. Turner, S. K. Spear, J. G. Huddleston, J. D. Holbrey and R. D. Rogers, *Green Chem*, 2003, 5, 443.
33 M. Wada, T. Kondo and T. Okano, *Polym J*, 2003, 35, 155.
34 G. Cheng, P. Varanasi, C. Li, H. Liu, Y. B. Melnichenko, B. A. Simmons, M. S. Kent and S. Singh, *Biomacromolecules*, 2011, 12, 933.
35 R. C. Remsing, R. P. Swatloski, R. D. Rogers and G. Moyna, *Chemical Communications*, 2006, 1271.
36 C. E. Wyman and N. D. Hinman, *Appl Biochem Biotech*, 1990, 24-5, 735.
37 F. Xu, J. Sun, N. V. S. N. M. Konda, J. Shi, T. Dutta, C. D. Scown, B. A. Simmons and S. Singh, *Energy & Environmental Science*, 2016.

Example 2

Glucose Yields from Biomass Pretreatment Using Phosphate-Based Ionic Liquids

The pretreatment of biomass using PBIL gives rise to results shown in Table 5. "N444" is 3-tri-n-butylammonium, and "Ch" is cholinium.

TABLE 5

IL results summary.

| ILs | | | | Solid | Composition | | | Enzymatic Saccharification |
|---|---|---|---|---|---|---|---|---|
| | Predicted net basicity | pH | T/t | recovery | Lignin % | Glucan % | Xylan % | Glucose yield % |
| [N444][H2PO4] | 0.7 | 4.5 | 50/3 | 86.1 | 18.6 | 39.6 | 21.6 | 13.4 ± 2.6 |
| | | | 90/3 | 86.6 | 18.8 | 37.7 | 21.1 | 16.2 ± 0.6 |
| [Ch]3[PO4] 20% | 6.1 | | 140/1 | 50 | 11.7 | 51.8 | 23.8 | 54.6 |
| [Ch]3[PO4] 50% | | | 140/1 | 46 | 4.6 | 61.5 | 18.8 | 61.1 |
| [Ch]3[PO4] 100% | | | 140/1 | 50 | 7.8 | 44.0 | 15.3 | 61.8 |
| [Ch]2[HPO4] 20% | 0.4 | | 140/1 | 60 | 17.9 | 47.6 | 21.9 | 61.9 |
| [Ch]2[HPO4] 50% | | | 140/1 | 50 | 15.9 | 48.7 | 21.7 | 55.1 |
| [Ch]2[HPO4] 100% | | | 140/1 | 50 | 13.0 | 51.8 | 18.7 | 49.7 |
| [Ch][H2PO4] 20% | | | 140/1 | 54 | 20.3 | 39.4 | 24.4 | 17.5 |
| [Ch][H2PO4] 50% | | | 140/1 | 46 | 18.5 | 37.8 | 22.6 | 16.9 |
| [Ch][H2PO4] 100% | | | 140/1 | 46 | 19.5 | 39.5 | 23.9 | 14.4 |
| [Ch][Bicarbonate] | 0.2 | | 140/1 | 60 | 12.6 | 48.7 | 22.8 | 52.8 ± 4.3 |
| dimethylammonium dimethylcarbamate | | | 140/1 | 49 | 9.3 | 45.0 | 24.0 | 55.2 ± 3.9 |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method to produce a pretreated biomass solution or slurry from a biomass, comprising: introducing (i) a protic ionic liquid (PIL) comprising the following structure: [α'][β'], wherein [α'] is an alkanol amine, a dialkanol amine, a trialkanol amine, a cholinium, or a mixture thereof, and [β'] is a phosphate-based anion, an unsubstituted alkanoate, a substituted alkanoate, a halide, a sulfate, or a mixture thereof, (ii) a phosphate-based ionic liquid (PBIL), or (iii) a mixture thereof, to a lignocellulosic biomass to produce a solution or slurry.

2. The method of claim 1, further comprising:
    incubating the solution or slurry at about 140° C. to 160° C. for about 30 minutes to 3 hours.

3. The method of claim 2, further comprising:
    introducing a cellulase to the solution or slurry.

4. The method of claim 3, further comprising: incubating the solution or slurry at about 50° C. for about 72 hours to produce sugars; and
    (e) introducing a yeast or *Escherichia coli* (*E. coli*) to the solution or slurry, wherein the yeast or *E. coli* produces a biofuel.

5. The method of claim 1, wherein [α'] is an ethanolamine, a diethanolamine, a triethanolamine, a cholinium, or a mixture thereof.

6. The method of claim 1, wherein PBIL has the following structure: [α][β], and wherein [α] is a substituted primary, secondary, tertiary, or quaternary alkylamine, or a mixture thereof, and [β] is a phosphate ($PO_4^{3-}$), a hydrogen phosphate ($HPO_4^{2-}$), a dihydrogen phosphate ($H_2PO_4^-$), or a mixture thereof.

7. The method of claim 6, wherein [α] is a cholinium, an ethyl amine, an ethanol amine, or a mixture thereof.

8. The method of claim 1, wherein the PIL or PBIL have a concentration having a value from about 10% to about 100%.

9. The method of claim 1, wherein the solution or slurry produced by the introducing step produces a glucose yield of equal to or more than 50%.

10. The method of claim 1, wherein the introducing step comprises introducing a protic ionic liquid (PIL) comprising the following structure: [α'][β'], and wherein [α'] is an ethanolamine, a diethanolamine, a triethanolamine, a cholinium, or a mixture thereof, and [β'] is phosphate-based anion, an unsubstituted alkanoate, a substituted alkanoate, a halide, a sulfate, or a mixture thereof, to a lignocellulosic biomass to produce a solution or slurry.

11. The method of claim 1, wherein the introducing is with a phosphate-based ionic liquid (PBIL) to a lignocellulosic biomass to produce a solution or slurry.

12. The method of claim 1, wherein the introducing step comprises introducing a mixture of (i) a protic ionic liquid (PIL) comprising the following structure: [α'][β'], and wherein α' is an ethanolamine, a diethanolamine, a triethanolamine, a cholinium, or a mixture thereof, and β' is phosphate-based anion, an unsubstituted alkanoate, a substituted alkanoate, a halide, a sulfate, or a mixture thereof, and (ii) a phosphate-based ionic liquid (PBIL), to a lignocellulosic biomass to produce a solution or slurry.

* * * * *